United States Patent
Johs

(10) Patent No.: US 7,268,876 B1
(45) Date of Patent: Sep. 11, 2007

(54) GENERAL VIRTUAL INTERFACE ALGORITHM FOR IN-SITU SPECTROSCOPIC ELLIPSOMETRIC DATA ANALYSIS

(75) Inventor: Blaine D. Johs, Lincoln, NE (US)

(73) Assignee: J.A. Woollam Co., Inc, Lincoln, NE (US)

( * ) Notice: Subject to any disclaimer, the term of this patent is extended or adjusted under 35 U.S.C. 154(b) by 742 days.

(21) Appl. No.: 10/713,816

(22) Filed: Nov. 17, 2003

Related U.S. Application Data

(60) Provisional application No. 60/485,009, filed on Jul. 5, 2003.

(51) Int. Cl.
*G01J 4/00* (2006.01)
*G01N 21/86* (2006.01)

(52) U.S. Cl. .................. 356/369; 250/559.09
(58) Field of Classification Search ................ 356/369, 356/364; 250/559.09, 225
See application file for complete search history.

(56) References Cited

U.S. PATENT DOCUMENTS

| | | | |
|---|---|---|---|
| 4,770,895 A | 9/1988 | Hartley | 427/10 |
| 4,934,788 A | 6/1990 | Southwell | 350/164 |
| 5,091,320 A * | 2/1992 | Aspnes et al. | 427/8 |
| 5,131,752 A * | 7/1992 | Yu et al. | 356/369 |
| 5,526,117 A | 6/1996 | Wielsch et al. | 356/369 |
| 5,582,646 A | 12/1996 | Woollam et al. | 118/708 |
| 5,929,995 A | 7/1999 | Johs | 356/369 |
| 6,573,999 B1 | 6/2003 | Yang | 356/632 |
| 2004/0257567 A1 * | 12/2004 | Woollam et al. | 356/369 |

OTHER PUBLICATIONS

"Optical Characterization of Continuous Compositional Gradients in Thin Films by Real Time Spectroscopic Ellipsometry", S. Kim and R.W. Collins, Appl. Phys. Lett. 67 (1995), 3010.

"Growth of $Al_xGa_{1-x}As$ Parabolic Quantum Wells by Real-Time Feedback Control of Composition", D.E. Aspnes, W.E. Quinn, M.C. Tamargo, M.A.A. Pudensi, S.A. Schwarz, M.J.S.P. Brasil, R.E. Nahory, and S. Gregory, Appl. Phys. Lett. 60 (1992), 2776.

"Real-time Control of the MBE Growth of InGaAs in InP", J.A. Roth, D.H. Chow, G.L. Olson, P.D. Brewer, W.S. Williamson, and B. Johs, J. Crystal Growth 201/202 (1999), 31.

"Status of HgCdTe-MBE Technology for Producing Dual-Band Infrared Detectors", R.D. Rajavel, P.D. Brewer, D.M. Jamba, J.E. Jensen, C. LeBeau, G.L. Olson, J.A. Roth, W.S. Williamson, J.W. Bangs, P. Goetz, J.L. Johnson, E.A. Patten, J.A. Wilson, J. Crystal Growth 214/215 (2000), 1100.

In Situ Multi-Wavelength Ellipsometric Control of Thickness and Composition for Bragg Reflection Structures, C. Herzinger, B. Johs, P. Chow, D. Reich, G. Carpenter, D. Croswell, and J. Van Hove, Mat. Res. Soc. Symp. Proc. vol. 406 (1996), 347.

(Continued)

*Primary Examiner*—Roy M. Punnoose
(74) *Attorney, Agent, or Firm*—James D. Welch

(57) ABSTRACT

A method of characterizing the outermost material on an article manufactured by deposition or removal of material from its surface, which requires no prior knowledge of the composition of the article.

24 Claims, 5 Drawing Sheets

OTHER PUBLICATIONS

"Closed-loop Control of Resonating Tunneling Diode Barier Thickness Using In Situ Spectroscopic Ellipsometry", J.A. Roth, W.S. Williamson, D.H. Chow, G.L. Olson, and B. Johs, J. Vac, Sci. Technol. B 18 (2000), 1439.

"In situ Spectral Ellipsometry for Real-Time Measurement and Control", W.M. Duncan and S.A. Henck, Appl. Surf. Sci. 63 (1993), 9.

"In Situ Ellipsometric Diagnosis of Multilayer Thin Film Deposition During Sputtering", X. Gao, D.W. Glenn, and J.A. Woollam, Thin Solid Films 313-314 (1998), 511.G.E. Jellison Jr., Thin Solid Films 234 (1993), 416. data, see references [9,10]).

"Spectroscopic Ellipsometry Data Analysis: Measurement Versus Calculated Quantities", G.E. Jellison Jr., Thin Solid Films 313-314 (1998), 511.

"Overview of Variable Angle Spectroscopic Ellipsometry (VASE), Part 1: Basic Theory and Typical Applications", J.A. Woollam, B. Johs, C.M. Herzinger, J. Hilfiker, R. Synowicki, and C. L. Bungay, SPIE Critical Reviews vol. CR72 (1999), 3.

"Minimal-data Approaches for Determining Outer-layer Dielectric Responses of Films From Kinetic Reflectometric and Ellipsometric Measurements", D.E. Aspnes, J. Opt. Soc. Amer. A 10 (1993), 974.

"Optical Approaches to Determine Near-Surface Compositions During Epitaxy", D.E. Aspnes, J. Vac. Sci. Technol. A 14 (1996), 960. F.K. Urban III and M.F. Tabet, J. Vac. Sci. Technol. A 11 (1993), 976.

"Virtual Interface Method for In Situ Ellipsometry fo Films Grown on Unknown Substrates", F.K. Urban III and M.F. Tabet, J. Vac. Sci. Technol. A 11 (1993), 976.

"Real Time Monitoring of the Growth of Transparent Thin Films by Spectroscopic Ellipsometry", M. Kildemo and B. Drevillon, Rev. Sci. Instrum. vol. 67, No. 5 (1996), 1957.

"Characterization of Quasi-Rugate Filters Using Ellipsometric Measurements", A.V. Tikhonravov, M.K. Trubetskov, J. Hrdina, and J. Sobota, Thin Solid Films 277 (1996), 83.

"Approximation of Reflection Coefficients for Rapid Real-time Calculation of Inhomogeneous Films", M. Kildemo, O. Hunderi, B. Drevillon, J. Opt. Soc. Am. A 14 (1997), 931.

"Real-time In Situ Ellipsometric Control of Antireflection Coatings for Semiconductor Laser Amplifiers Using $SiO_x$", I-Fan Wu, J.B. Dottellis, M. Dagenais, J. Vac. Sci. Technol. A 11 (1993), 2398.

"Real Time Control of Plasma Deposited Optical Filters by Multiwavelength Ellipsometry", T. Heitz, A. Hofrichter, P. Bulkin, and B. Drevillon, J. Vac. Sci. Technol. A 18 (2000), 1303.

"Direct Numerical Inversion Method for kinetic Ellipsometry Data. 1. Presentation of the Method and Numerical Evaluation", D. Kouznetsov, A. Hofirchter, and B Drevillon, Appl. Opt. 41 (2002) 4510.

"Recherches Sur La Propagation Des Ondes Electromagnetiques Sinusoidales Dans Les Milieuc Stratifies Application Aux Couches Minces", F. Abeles, Ann. De Physique, 5 (1950) 596.

Model M2000X, J.A. Woollam Co., Inc., Lincoln, NE USA.

"Data Analysis for Spectroscopic Ellipsometry", G.E. Jellison Jr., Thin Solid Films, 234, 1993, 416-422.

"In situ and Ex Situ Applications of Spectroscopic Ellipsometry", J. A. Woollam, B. Johs, W. McGahan, P. Snyder, J. Hale, H. Yao, Mat. Res. Soc. Proc., vol. 324, 1994, p. 15.

* cited by examiner

GENERAL VIRTUAL INTERFACE ALGORITHM FOR IN-SITU SPECTROSCOPIC ELLIPSOMETRIC DATA ANALYSIS

This Application Claims benefit of Provisional Application Ser. No. 60/485,009, Filed Jul. 5, 2003.

This work was partially supported under NIST ATP Agreement #70NANBOH3048. The U.S. Government might have certain rights in the invention.

TECHNICAL FIELD

The disclosed invention relates to methods of characterizing articles during manufacture, and more particularly is a method of characterizing the outermost material on a process substrate manufactured by deposition or removal of material, to or from, its surface, which method requires no prior knowledge of the composition of the article.

BACKGROUND

It is known to investigate thin surface layers on objects with spectroscopic electromagnetic radiation. Typically a mathematical model of the system is proposed for the entire system, and is data obtained corresponding to change in polarization state in a beam of electromagnetic radiation caused to interact with the system. A regression procedure is then performed to modify the values of parameters in the mathematical model to bring calculated results into agreement with measured data.

In some cases, however, the state of a sample as obtained, or entered into analysis, is initially unknown and proposing a mathematical model therefore is not possible. For instance, it comprises a substrate which was subjected to previous processing, the specific nature of which is unknown. This can be the case, for instance, where articles are manufactured via deposition or removal of material, to or from, a process substrate.

With the invention disclosed in this Specification in mind, prior art of varying degrees of relevance was identified.

Known Patents are:
- U.S. Pat. No. 4,770,895 to Hartley is disclosed as it describes a application of ellipsometry controlling growth of alloy films.
- U.S. Pat. No. 5,091,320 to Aspnes is disclosed as it describes application of ellipsometry to controlling material growth.
- U.S. Pat. No. 5,626,117 to Wielsch et al. is disclosed as it describes a method for determining characteristic values of transparent layers using ellipsometry.
- U.S. Pat. No. 5,582,646 to Woollam et al., is disclosed as it describes a system for applying ellipsometry to investigate samples.
- U.S. Pat. No. 5,929,995 to Johs is disclosed as it describes a system for use in directing beams in process chambers.
- U.S. Pat. No. 6,573,999 to Yang is disclosed as it describes determining film thickness using light absorption of material underlying a film.
- U.S. Pat. No. 4,934,788 to Southw 11 is disclosed as it describes deposition of coatings using rate control.

Known articles are disclosed in a bibliography format, as they are referred to throughout the Specification by the identifying number.

1. "Optical Characterization of Continuous Compositional Gradients in Thin Films by Real Time Spectroscopic Ellipsometry", S. Kim and R. W. Collins, Appl. Phys. Lett. 67 (1995), 3010.
2. "Growth of $Al_xGa_{1-x}As$ Parabolic Quantum Wells by Real-Time Feedback Control of Composition", D. E. Aspnes, W. E. Quinn, M. C. Tamargo, M. A. A. Pudensi, S. A. Schwarz, M. J. S. P. Brasil, R. E. Nahory, and S. Gregory, Appl. Phys. Lett. 60 (1992), 1244.
3. "Real-time Control of the MBE Growth of InGaAs in InP", J. A. Roth, D. B. Chow, G. L. Olson, P. D. Brewer, W. S. Williamson, and B. Johs, J. Crystal Growth 201/202 (1999), 31.
4. "Status of HgCdTe-MBE Technology for Producing Dual-Band Infrared Detectors", R. D. Rajavel, P. D. Brewer, D. M. Jamba, J. E. Jensen, C. LeBeau, G. L. Olson, J. A. Roth, W. S. Williamson, J. W. Bangs, P. Goetz, J. L. Johnson, E. A. Patten, J. A. Wilson, J. Crystal Growth 214/215 (2000), 1100.
5. In Situ Multi-Wavelength Ellipsometric Control of Thickness and Composition for Bragg Reflection Structures", C. Horzinger, B. Johs, P. Chow, D. Roich, G. Carpenter, D. Croswell, and J. Van Hove, Mat. Res. Soc. Symp. Proc. Vol. 406 (1996), 347.
6. "Closed-loop Control of Resonating Tunneling Diode Barrier Thickness Using In Situ Spectroscopic Ellipsometry", J. A. Roth, W. S. Williamson, D. H. Chow, G. L. Olson, and B. Jobs, J. Vac. Sci. Technol. B 18 (2000), 1439.
7. "In situ Spectral Ellipsometry for Real-Time Measurement and Control", W. M. Duncan and S. A. Henck, Appl. Surf. Sci. 63 (1993), 9.
8. "In Situ Ellipsometric Diagnosis of Multilayer Thin Film Deposition During Sputtering", X. Gao, D. W. Glenn, and J. A. Woollam, Thin Solid Films 313-314 (1998), 511. G. E. Jellison Jr., Thin Solid Films 234 (1993), 416.
9. "Spectroscopic Ellipsometry Data Analysis: Measurement Versus Calculated Quantities", G. E. Jellison Jr., Thin Solid Films 313-314 (1998), 511.
10. "Overview of Variable Angle Spectroscopic Ellipsometry (VASE), Part 1: Basic Theory and Typical Applications", J. A. Woollam, B. Johs, C. M. Herzinger, J. Hilfiker, R. Synovicki, and C. L. Bungay, SPIE Critical Reviews Vol. CR72 (1999), 3.
11. "Minimal-data Approaches for Determining Outer-layer Dielectric Responses of Films From Kinetic Reflectometric and Ellipsometric Measurements", D. E. Aspnes, J. Opt. Soc. Amer. A 10 (1993), 974.
12. "Optical Approaches to Determine Near-Surface Compositions During Epitaxy", D. E. Aspnes, J. Vac. Sci. Technol. A 14 (1996), 960. F. K. Urban III and M. F. Tabet, J. Vac. Sci. Technol. A 11 (1993), 976.
13. "Virtual Interface Method for In Situ Ellipsometry to Films Grown on Unknown Substrates", F. K. Urban III and M. F. Tabet, J. Vac. Sci. Technol. A 11 (1993), 976.
14. "Real Time Monitoring of the Growth of Transparent Thin Films by Spectroscopic Ellipsometry", M. Kildemo and B. Drevillon, Rev. Sci. Instrum. Vol. 67, No. 5 (1996), 1957.
15. "Characterization of Quasi-Rugate Filters Using Ellipsometric Measurements", A. V. Tikhonravov, M. K. Trubetskov, J. Hrdina, and J. Sobota, Thin Solid Films 277 (1996), 83.
16. "Approximation of Reflection Coefficients for Rapid Real-time Calculation of Inhomogeneous Films", M. Kildemo, O. Hunderi, B. Drevillon, J. Opt. Soc. Am. A 14 (1997), 931.

17. "Real-time In Situ Ellipsometric Control of Antireflection Coatings for Semiconductor Laser Amplifiers Using $SiO_x$", I-Fan Wu, J. B. Dottellis, M. Dagenais, J. Vac. Sci. Technol. A 11 (1993), 2398.
18. "Real Time Control of Plasma Deposited Optical Filters by Multiwavelength Ellipsometry", T. Heitz, A. Hofrichter, P. Bulkin, and B. Drevillon, J. Vac. Sci. Technol. A 18 (2000), 1303.
19. "Direct Numerical Inversion Method for kinetic Ellipsometry Data. 1. Presentation of the Method and Numerical Evaluation", D. Kouznetsov, A. Hofirchter, and B Drevillon, Appl. Opt. 41 (2002) 4510.
20. "Recherches Sur La Propagation Des Ondes Electromagnetiques Sinusoidales Dans Les Milieuc Stratifies Application Aux Couches Minces", F. Abeles, Ann. De Physique, 5 (1950) 596.
21. "Thin-Film Optical Filters", H. A. Macleod, McGraw-Hill, New York N.Y., 1989, p. 40.
22. "Ellipsometry and Polarized Light", R. M. A. Azzam and N. M. Bashara, North-Holland, Amsterdam, 1977.
23. "Numerical Recipes in C", W. H. Press, B. P. Flannery, S. A. Teukolsky, and W. T. Vetterling, Cambridge University Press, Cambridge, 1988.
24. Model M2000X, J. A. Woollam Co., Inc., Lincoln, NE USA.
25. "Data Analysis for Spectroscopic Ellipsometry", G. E. Jellison Jr., Thin Solid Films, 234, 1993, 416-422.
26. "In situ and Ex Situ Applications of Spectroscopic Ellipsometry", J. A. Woollam, B. Johs, W. McGahan, P. Snyder, J. Hale, H. Yao, Mat. Res. Soc. Proc., Vol 324, 1994, p. 15.

Even in view of the known prior art, need remains for a method of characterizing the outermost material on an article manufactured by deposition or removal of material to or from its surface, which method requires no prior knowledge of the composition of the article.

DISCLOSURE OF THE INVENTION

In a general sense, the disclosed invention is a method of ellipsometrically characterizing surface material present on an article manufactured by the deposition or removal of material, to or from, a process substrate, said method requiring no explicit knowledge of prior process substrate composition. Said method is generally understood as comprising the steps of:

a) providing a material deposition and/or removal chamber, and an ellipsometer system configured with respect thereto so as to, in use, cause a beam of electromagnetic radiation to impinge upon an article therewithin during a procedure in which material deposition to, or removal from, a process substrate is caused to occur over a period of time:

a') at least two times causing said ellipsometer system to cause a beam of electromagnetic radiation to impinge upon the article such that sufficient ellipsometric data to evaluate variable parameters which characterize the optical response of the article;

a") in conjunction with the foregoing steps, providing a system of variable parameter containing analytic equations which describe interaction of electromagnetic radiation with a layered material system;

b) utilizing said sufficient ellipsometric data obtained in step a' and said system of variable parameter containing analytic equations provided in a", to predict ellipsometric characterization of said article at a prediction time which is different from either of said at least two times of step a';

c) during material deposition or removal, to or from, a process substrate, obtaining ellipsometric data at a time corresponding to the prediction time of stop b; and d) utilizing said ellipsometric data obtained in step c in a minimization algorithm to provide values for the variable parameters in at least one selection from the group consisting of:

said variable parameters in said variable parameter containing analytic equations which describe interaction of electromagnetic radiation with a layered material system provided in step a"; and said variable parameters identified in step a' which characterized the optical response of the article;

at said prediction time in step b;

and interpreting the resulting values for said variable parameters to characterize surface material of said article at the time data was obtained in step c.

A more specific recital of the disclosed invention method of characterizing the outermost material of an article manufactured by the deposition or removal of material, to or from, a process substrate, without explicit knowledge of any previously deposited underlying layers, comprises the steps of:

a) providing a material deposition or removal chamber and an ellipsometer system configured with respect thereto so as to, in use, cause a beam of polarized electromagnetic radiation to impinge upon a process substrate therewithin during a procedure in which material deposition or removal upon said process substrate is caused to occur over a period of time;

a') obtaining ellipsometric data during material deposition or removal upon said process substrate at three distinct times (t1), (t2), and (t3);

b) using a system of analytic equations which are derived from the exact Fresnel equations that describe the interaction of electromagnetic radiation with a layered material system, such analytic equations not requiring any knowledge of the underlying layer structure previously deposited on the sample, calculating ellipsometric data at time (t3), using the ellipsometric data acquired at times (t1) and (t2), and a parameterized optical model for the outermost material deposition or removal that occurs between (t1) and (t3), and (t2) and (t3);

c) determining the optical model parameters which characterize the outermost layer(s) by minimizing the difference between the ellipsometric data calculated at time (t3) by the analytical equations in b) and the ellipsometric data measured at time (t3), using a minimization algorithm.

Note that the foregoing method specifically requires that data be obtained at Three (3) different times. The following recites disclosed invention methodology for the case in which data is obtained at Four (4) different times.

A method of characterizing the outermost material of an article manufactured by the deposition or removal of material, to or from, a process substrate, without explicit knowledge of any previously deposited underlying layers, comprising the steps of:

a) providing a material deposition or removal chamber and an ellipsometer system configured with respect thereto so as to, in use, cause a beam of polarized electromagnetic radiation to impinge upon a process substrate therewithin during a procedure in which material deposition or removal upon said process substrate is caused to occur over a period of time;

a') obtaining ellipsometric data during material deposition or removal upon said process substrate at four distinct times (t1), (t2), (t3), and (t4);

b) using a system of analytic equations which are derived from the exact Fresnel equations that describe the interaction of electromagnetic radiation with a layered material system, such analytic equations not requiring any knowledge of the underlying layer structure previously deposited on the sample, calculating ellipsometric data:

at time (t1), using the ellipsometric data acquired at times (t2) and (t4), and a parameterized optical model for the outermost material deposition or removal that occurs between (t1) and (t2), and (t1) and (t4);

at time (t2), using the ellipsometric data acquired at times (t1) and (t3), and a parameterized optical model for the outermost material deposition or removal that occurs between (t2) and (t1), and (t2) and (t3);

at time (t3), using the ellipsometric data acquired at times (t2) and (t4), and a parameterized optical model for the outermost material deposition or removal that occurs between (t3) and (t2), and (t3) and (t4);

at time (t4), using the ellipsometric data acquired at times (t1) and (t3), and a parameterized optical model for the outermost material deposition or removal that occurs between (t4) and (t1), and (t4) and (t3);

c) determining the optical model parameters which characterize the outermost layer(s) by minimizing the differences between the ellipsometric data calculated at times (t1), (t2), (t3), and (t4) by the analytical equations in b) and the ellipsometric data measured at times (t1), (t2), (t3), and (t4) using a minimization algorithm.

The following recites the disclosed invention methodology for the case in which data is obtained at more than Three different times.

A method of characterizing the outermost material of an article manufactured by the deposition or removal of material, to or from, a process substrate, without explicit knowledge of any previously deposited underlying layers, comprising the steps of:

a) providing a material deposition or removal chamber and an ellipsometer system configured with respect thereto so as to, in use, cause a beam of polarized electromagnetic radiation to impinge upon a process substrate therewithin during a procedure in which material deposition or removal upon said process substrate is caused to occur over a period of time;

a') obtaining ellipsometric data during material deposition or removal upon said process substrate at least three distinct times {t1, t2, t3 . . . tn};

b) using a system of analytic equations which are derived from the exact Fresnel equations that describe the interaction of electromagnetic radiation with a layered material system, such analytic equations not requiring any knowledge of the underlying layer structure previously deposited on the sample, calculating ellipsometric data:

at one time selected from the set of ellipsometric data points chosen in a'), using the ellipsometric data acquired at two other times from the set of ellipsometric data points chosen in a'), and a parameterized optical model for the outermost material deposition or removal that occurs between the selected times;

optionally at additional times selected from the set of ellipsometric data points chosen in a'), using the ellipsometric data acquired at two other times from the set of ellipsometric data points chosen in a'), and a parameterized optical model for the outermost material deposition or removal that occurs between the selected times;

c) determining the optical model parameters which characterize the outermost layer(s) by minimizing the differences between the ellipsometric data calculated at the selected times by the analytical equations in b) and the ellipsometric data measured at the selected times using a minimization algorithm.

The minimization algorithm can be implemented by non-linear regression, and preferably the minimization algorithm is the Levenberg-Marquardt method.

The optical model for the outermost material deposition or removal can be parameterized by at least one of the parameters from the selected list:
the material deposition rate,
the material removal rate,
the optical constants of the outermost material,
the surface roughness of the outermost material.

The process substrate can be of a shape selected from the group consisting of:
comprising a planar surface;
of an arbitrary shape.

Finally is to be understood that the method step of obtaining ellipsometric data can be characterized by at least one selection from the group consisting of:
it is acquired at a single wavelength;
it is acquired at a more than one wavelength;
it is acquired at a single angle of incidence;
it is acquired at least two angles of incidence of the ellipsometric electromagnetic beam to the surface of the process substrate.

The disclosed invention will be better understood by reference to the Detailed Description Section of this Specification, with reference to the Drawings.

SUMMARY

It is therefore a purpose and/or objective of the disclosed invention to teach a new general virtual interface algorithm for the analysis of in situ Spectroscopic Ellipsometric data.

It is another purpose and/or objective of the disclosed invention to teach an algorithm which is "general" in two senses:

1) exact thin film optical equations are used, such that it can be applied to the deposition of any material (semiconductor, metal, or dielectric), and over any time/thickness range, and 2) any arbitrary isotropic layer structures, including surface roughness, index gradients, etc. (excepting depolarizing structures such as incoherent backside reflections from substrates) can be incorporated into the analysis.

It is yet another purpose and/or objective of the disclosed invention to teach a method of characterizing the outermost material on an article manufactured by deposition or removal of material from its surface, which requires no prior knowledge of the composition of the article.

Additional purpose and/or objective of the disclosed invention will become apparent upon a reading of the Specification and Claims.

DETAILED DESCRIPTION

A more detailed presentation, in conduction with the Drawings follows directly. It is first noted in the following, numbers inside [ ] refer to references corresponding to said numbers listed in the Background Section of this Disclosure.

The basis of the disclosed invention is a General Virtual Interface (GenVI) algorithm, derived for in situ spectroscopic ellipsometry (SE) data analysis. Importantly, said new algorithm is applicable to any material deposition (ie. semiconductor, metal, or dielectric etc.), to determine the topmost layer thickness, complex index of refraction, and surface roughness, completely independent of the previous deposition history. Exact thin film equations are used in the calculation, which allows wider time ranges of data to be incorporated into the analysis, thereby improving the precision and accuracy of the results (compared to derivative-based approaches). The effectiveness of said GenVI algorithm is demonstrated by the analysis of in situ SE data acquired during the deposition of a DLC film on a metal process substrate, under particularly challenging, (ie. real-world), experimental conditions.

Figure 1:
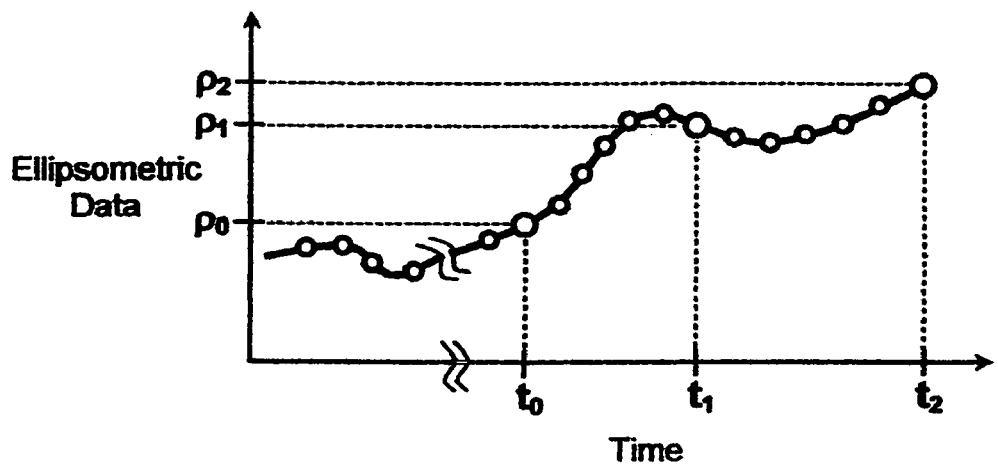
FIG. 1 is a Schematic representation of in situ ellipsometric data at a single wavelength, (expressed in complex reflectivity ratio (ρ format), as a function of time. The circles represent discrete ellipsometric data points. The large circles are selected data points at times t0, t1, and t2, and correspond to stages in the sample deposition depicted in FIG. 2.
Figure 2:
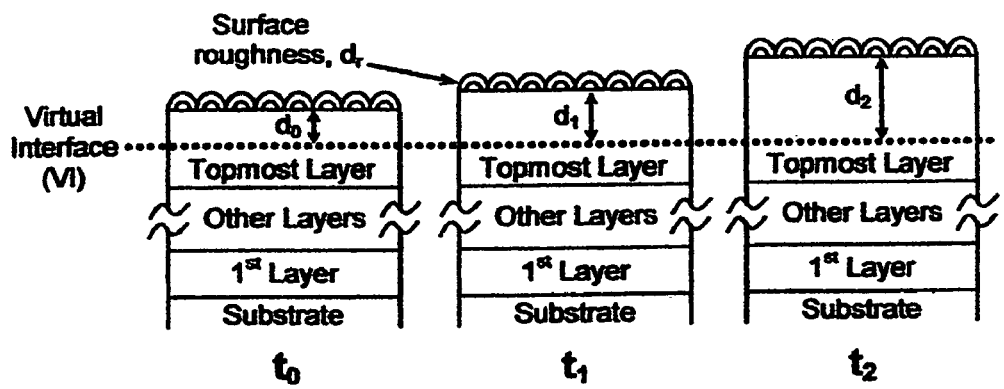
FIG. 2 is a Schematic representation of the Virtual Interface (VI) concept, illustrating changes in the sample structure above the VI at times t0, t1, and t2. The VI can be located anywhere within the sample structure, and does not necessarily correspond to a real material interface.

Compared to ex situ ellipsometry, which is limited to observation of the sample's final state, in situ ellipsometry can collect data throughout the entire process. This is schematically depicted in FIG. 1. While in situ ellipsometry provides a wealth of data, analysis is required to extract the desired material properties from the raw ellipsometric data. Traditionally, a layered optical model is used to analyze SE data, (see Background references [9,10]). While this approach works extremely well for simple and ideal samples, the analysis can become particularly difficult for complex multiple layer samples (some optical coatings contain 10's or even 100's of layers), films with index gradients (intentional or non-intentional), or samples in which the optical properties of the process substrate and/or interfacial layers are not well known. Furthermore, real-time in situ SE process monitoring and control applications would be greatly simplified by a data analysis approach that could provide the material properties, (index, composition, deposition rate, surface roughness, etc.), of the most recently deposited film, without requiring any a priori information about the underlying, (previously deposited), sample structure. With this goal in mind, many in situ ellipsometry "near surface" data analysis algorithms have been developed, (see Background references [11-19]). Many of these algorithms utilize the concept of a Virtual Interface (VI), which is illustrated in FIG. 2. Below the VI is the underlying sample structure, which is not required for the analysis and is assumed to remain unchanged during subsequent film deposition; and above the VI is the recently deposited, topmost, (ie. near the surface), layer which is to be characterized. To characterize said near surface region of the film, the VI is typically "tracked" to remain at a fixed time below the surface of the film as the deposition proceeds. The "depth" of the VI is determined by the time spacing between the in situ SE data points included in the analysis and the deposition rate of the film. Virtual interface (VI) algorithms based on the Common Pseudo-Substrate Approximation (CPA), (see Background references [11-12]), have successfully extracted the near-surface optical response from in situ ellipsometric data and been applied in many semiconductor deposition monitoring and control applications. However, it is widely recognized that the simplifying assumption used by the CPA to calculate the VI parameters is not universally valid, (see Background references [14, 16, 19]), and in particular it does not work for analyzing dielectric stacks typical of optical coatings applications. The general VI (GenVI) formulation presented here is valid for any material deposition (semiconductor, metal, dielectric etc.). The derivation is similar to that of Urban, (see Background reference [13]), in that exact thin film equations are used in the calculation. However, in the presently disclosed invention case, a minimum of only 3 dynamic data points are required in the analysis, and the algorithm is specifically formulated to facilitate robust regression of spectroscopic data.

Derivation of the General Virtual Interface (GenVI) Algorithm

The derivation of the GenVI algorithm presented here is based on the thin film calculation method first proposed by Abeles, (see Background reference [20]), and uses the optical admittance notation given in Macleod, (see Background reference [21]). Like most isotropic thin film calculation methods, 2×2 matrix algebra is used to describe the propagation of light through a layered optical structure. Separate calculations are performed for p- and s-polarized light, and ellipsometric quantities are computed from the ratio of the calculated p- and s-reflectivities. In the Macleod notation, the state of the propagating wave at any location within the optical structure is given by the optical admittance Y, which is defined as the ratio of the magnetic and electric fields. The goal of the GenVI algorithm is to calculate, at a specified location in the optical structure (denoted the "virtual interface", or VI), the optical admittances for p- and s-polarized light, Vp and Vs. Once the p- and s-admittances at the VI are known, ellipsometric data can be generated for any layer structure above the VI. The thin film calculation method is summarized in eqns. 1-6, (for more details, consult Background reference [21])). Eqn. 1 shows that given the input admittance Vp,s at a given location in the optical structure, the output admittance at a second location in the structure Yp,s can be calculated by multiplying the input admittance vector times the product of the characteristic matrices [$m_{p,s}$] of the n intervening layers. The elements of the characteristic matrix for the jth layer are defined in eqn. 2, in which the complex index of refraction for the jth layer is $$[m_{j_{p,s}}] = \begin{bmatrix} \cos\delta_j & i\sin\delta_j/y_{j_{p,s}} \\ y_{j_{p,s}}i\sin\delta_j & \cos\delta_j \end{bmatrix}$$

(according to the convention $\tilde{n} = n - ik$), the layer thickness is $d_j$, and the wavelength of light is $\lambda$. The propagation angle within the layer $\delta_j$ is calculated by eqn. 3 (as deduced from Snell s law, with the input beam angle of incidence q0). The tilted p- and s-optical admittances for each layer are defined according to equation 4. The complex p- and s-reflectivities can be calculated from eqn. 5, in which $y_{0_{p,s}}$ are the admittance values for the ambient (calculated using eqn. 4). Note the minus sign in the $r_p$ formula; this is due to a difference in coordinate system between Macleod and the traditional ellipsometry definition, (see Background reference [22]). Ellipsometric quantities $\Psi$, $\Delta$, the complex reflectivity ratio ($\rho$), N, C, and S are then given by eqns. 6 and 7.

$$\begin{bmatrix} B_{p,s} \\ C_{p,s} \end{bmatrix} = \left(\prod_{j=1}^{N}[m_{j_{p,s}}]\right)\begin{bmatrix} 1 \\ V_{p,s} \end{bmatrix} = [M_{p,s}]\begin{bmatrix} 1 \\ V_{p,s} \end{bmatrix} = \begin{bmatrix} M_{11_{p,s}} & M_{12_{p,s}} \\ M_{21_{p,s}} & M_{22_{p,s}} \end{bmatrix}\begin{bmatrix} 1 \\ V_{p,s} \end{bmatrix}, \quad (1)$$

$$Y_{p,s} = \frac{B_{p,s}}{C_{p,s}}$$

$$[m_{j_{p,s}}] = \begin{bmatrix} \cos\delta_j & i\sin\delta_j/y_{j_{p,s}} \\ y_{j_{p,s}}i\sin\delta_j & \cos\delta_j \end{bmatrix}, \delta_j = 2\pi\tilde{n}_j\cos\theta_j\frac{d_j}{\lambda} \quad (2)$$

$$\cos\theta_j = \sqrt{1 - \sin\theta_0/\tilde{n}_j^2} \quad (3)$$

$$y_{j_p} = \tilde{n}_j/\cos\theta_j, \; y_{j_s} = \tilde{n}_j\cos\theta_j \quad (4)$$

$$r_p = \frac{y_{0_p} - Y_p}{y_{0_p} + Y_p}, \; r_s = \frac{y_{0_s} - Y_s}{y_{0_s} + Y_s} \quad (5)$$

$$\rho = \frac{r_p}{r_s} = \tan\Psi e^{i\Delta} \quad (6)$$

$$N = \cos 2\Psi = \frac{2}{1+|\rho|^2} - 1, \; C = \sin 2\Psi \cos\Delta = \frac{2Re(\rho)}{1+|\rho|^2}, \quad (7)$$

$$S = \sin 2\Psi \sin\Delta = \frac{2Im(\rho)}{1+|\rho|^2}$$

Since two complex parameters (Vp and Vs) are required to fully characterize the virtual interface, the VI parameters can be calculated from two ellipsometric data points (each ellipsometric data point consists of two real values, e.g., ($\Psi$) and ($\Delta$), or can be expressed as a complex number ($\rho$), acquired at times t1 and t2. The two measured ellipsometric data points are denoted $\rho_1$ and $\rho_2$ (see eqn. 6 and 7 for conversions between common representations of ellipsometric data). The virtual interface itself could be located at any time tVI within the sample structure, but for the purpose of clarity in this discussion we will assume tVI=t0. Note that t0, t1, and t2 do not have to be evenly spaced or monotonic in time, but they must specify unique times, and for real-time data analysis, one of the times should correspond to the most recently acquired data point. The derivation begins by assuming that the product of characteristic matrices for the layer(s) representing the sample structure between the virtual interface and the top surface of the film at times t1 and t2 can be calculated. In the simplest case (a uniform film with no surface roughness, deposited at a constant rate), this requires a nominal index of refraction and deposition rate for the topmost film. Combining eqns. 1, 5, and 6 and collecting terms, provides that the ellipsometric data points $\rho_1$ and $\rho_2$ can be written as a function of the VI admittances in the form of eqn. 8, in which the Kxy "constants" are defined by eqns. 9 and 10. In eqn. 10, the $y_{0_{p,s}}$ value are the admittances for the ambient (calculated using eqn. 4), and the $M_{xy^i_{p,s}}$ values correspond to the characteristic matrix elements for the i'th data point, according to the format defined in eqn. 1.

$$\rho_i = \frac{K_{1i} + K_{2i}V_p + K_{3i}V_s + K_{4i}V_pV_s}{K_{5i} + K_{6i}V_p + K_{7i}V_s + K_{8i}V_pV_s}, i = 1, 2 \quad (8)$$

Eqn. 8 defines a system of two complex equations and two complex unknowns, which can be solved for the VI admittances Vp and Vs (eqns. 11 and 13). In eqn. 11, it can not be determined a-priori which of the two roots for the VI admittances is correct. However, the "best" root can be determined by using the VI admittance roots, (and eqns. 1 and 6), to calculate ellipsometric data at the third point in time t0 and choosing the root which generates data closest, (in a least squares sense), to the experimental ellipsometric data measured at that time ($\rho_0$).

$$V_s = \frac{-b \pm \sqrt{b^2 - 4ac}}{2a}, \quad V_p = \frac{C_1 + C_2 V_s}{C_3 + C_4 V_s} \quad (11)$$

$$a = \rho_2(K_{72}C_4 + K_{82}C_2) - (K_{32}C_4 + K_{42}C_2) \quad (12a)$$

$$b = \rho_2(K_{52}C_4 + K_{62}C_2 + K_{72}C_3 + K_{82}C_1) - (K_{12}C_4K_{22}C_2 + K_{32}C_3K_{42}C_1) \quad (12b)$$

$$c = \rho_2(K_{52}C_3 + K_{62}C_1) - (K_{12}C_3 + K_{22}C_1) \quad (12c)$$

$$C_1 = \rho_1 K_{51} - K_{11}, \quad C_2 = \rho_1 K_{71} - K_{31}, \quad C_3 = K_{21} - \rho_1 K_{61},$$
$$C_4 = K_{41} - \rho_1 K_{81} \quad (13)$$

Stated alternatively, eqns. (1-13) enable the calculation of generated ellipsometric data at a time t0, (the VI admittances Vp and Vs can be considered as intermediate variables in this calculation), given experimental ellipsometric data points $\rho_1$ and $\rho_2$, and the topmost film index and deposition rate. To complete the basic Three (3) point GenVI algorithm, a $\pi^2$ figure of merit function is defined (eqn. 14, in which G represents the GenVI calculation embodied by eqns. 1-13), the film index "n" and deposition rate "r" are defined as fitting parameters, and adjusted via non-linear regression (eg., the Levenberg-Marquardt algorithm, (see Background reference [23])), to minimize the difference between the calculated and experimental ellipsometric data at t0.

$$\chi^2 = [G(t_0, \rho_1, \rho_2; n, r) - \rho_0]^2 \quad (14)$$

Figure 3:
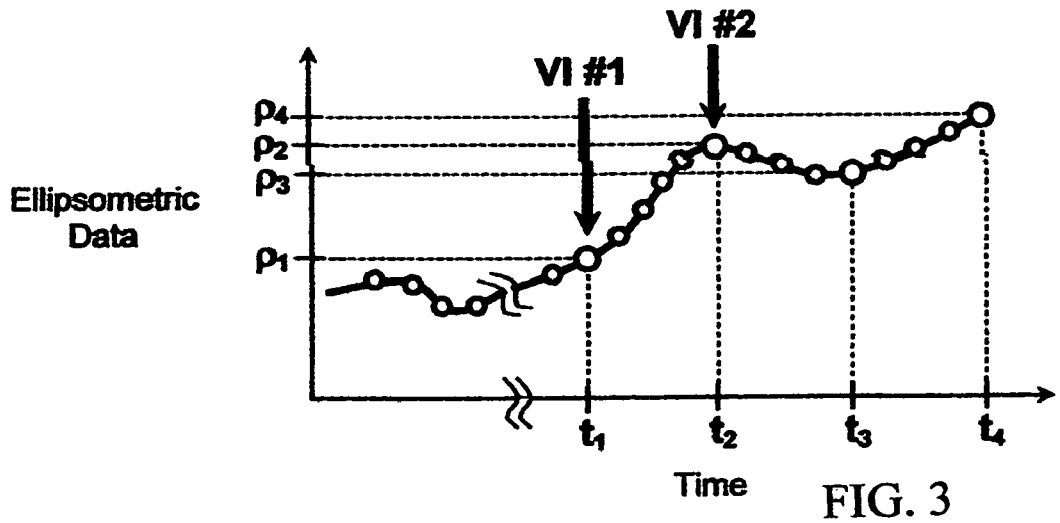
FIG. 3 is an Illustration of a 4 point GenVI algorithm: data points $\rho_2$ and $\rho_4$ are used to define VI#1, $\rho_1$ and $\rho_3$ define VI#2.

More complex GenVI analysis approaches can be constructed, using the basic Three (3) point algorithm as a building block. For example, a Four (4) point algorithm has been developed to provide robust analysis of in situ SE data, as will be demonstrated in the next section of the paper. A schematic of the Four (4) point algorithm is shown in FIG. 3. In this algorithm, two virtual interfaces are defined, using two combinations of non-adjacent data points. Generated data can then be calculated at the each of the four times and compared with the experimental data, (i.e., data at t1 and t3 are generated from VI #1 defined by t2 and t4; data at t2 and t4 are generated from VI #2 defined by t1 and t3). A $\chi^2$ merit function for the 4 point algorithm, extended to include a spectroscopic data set containing n wavelengths, is given by eqn. 15.

$$\chi^2 = \sum_{i=1}^{n} [(G(t_1, \rho_{2p}\rho_{3s}, n, r) - \rho_{1s})^2 + (G(t_2, \rho_{1p}\rho_{3s}, n, r) - \rho_{2s})^2 + (G(t_3, \rho_{2p}\rho_{3s}, n, r) - \rho_{3s})^2 + (G(t_4, \rho_{1p}\rho_{3s}, n, r) - \rho_{4s})^2] \quad (15)$$

The Four (4) point algorithm improves the robustness of the GenVI analysis for a number of reasons:
1) more data points are included in the analysis, which better defines the shape of the ellipsometric data vs. time curve,
2) two data points are generated from each VI (and compared to corresponding experimental data), which enables a better choice of the correct VI admittance root, and
3) all the data points are incorporated in a more symmetric, self consistent manner into the analysis, i.e., each point is used to both define a VI, and included as a data point in the $\chi^2$ merit function.

GenVI analysis results can be further improved by reducing the noise on the $\rho_i$ data points via polynomial smoothing of adjacent data points, and by adding error bars to properly weight each data point in the $\chi^2$ merit function, (see Background reference [9]). Other algorithms which relax the assumption of constant deposition rate and film index, or add surface roughness to the model, can be readily implemented by appropriately calculating the characteristic layer matrices which describe the light propagation between the VI and the $\rho_i$ data points (eqns. 1, 2, 10). More time points can be incorporated into the analysis by simply adding terms to the $\chi^2$ merit function (eqn. 15).

Testing of the General Virtual Interface (GenVI) Algorithm

Figure 4:
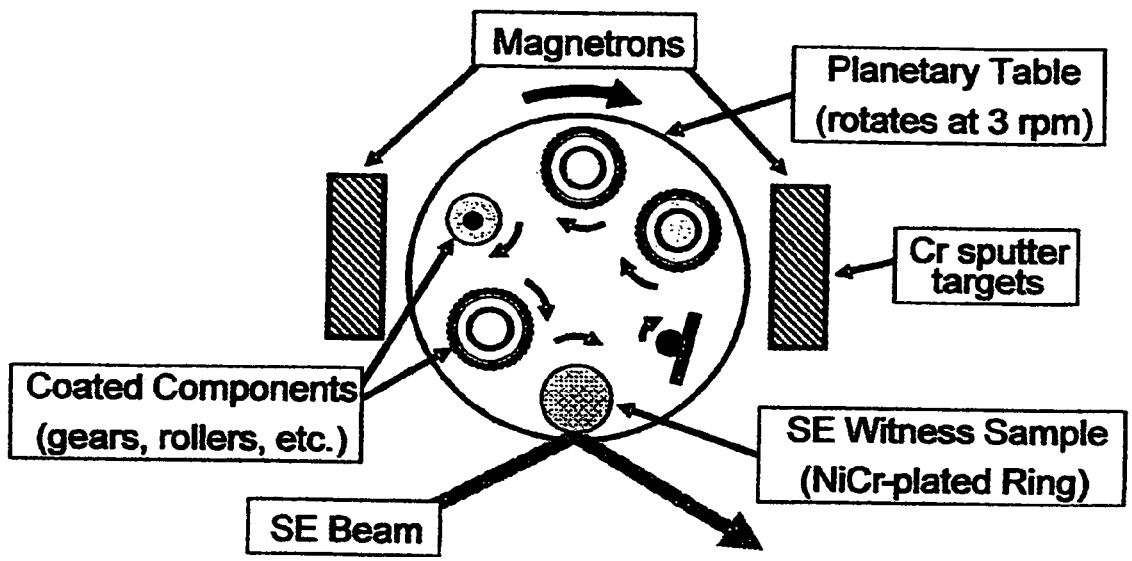
FIG. 4 is a Schematic of dual magnetron PECVD sputter chamber with planetary rotation mechanism. The table rotates at 3 rpm, while the gears, rollers, and SE witness sample, (i.e., the "planets") rotate at ⅓ rpm.
Figure 5:
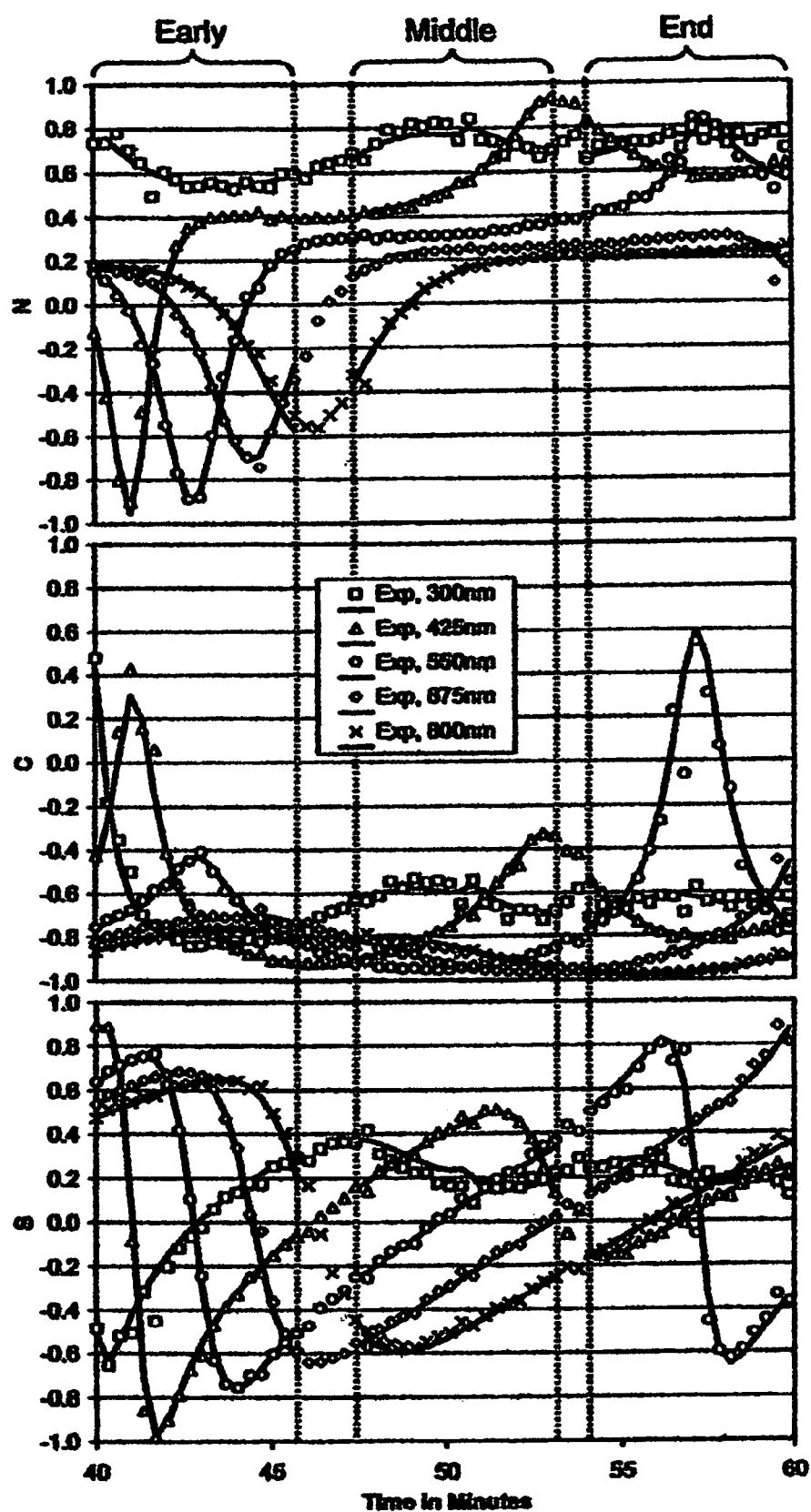
FIG. 5 shows a GenVI fits (solid curves) to in situ SE data (symbols) acquired during DLC film deposition. Results from three data fits are shown near the early, middle, and end stages of deposition.
Figure 6:
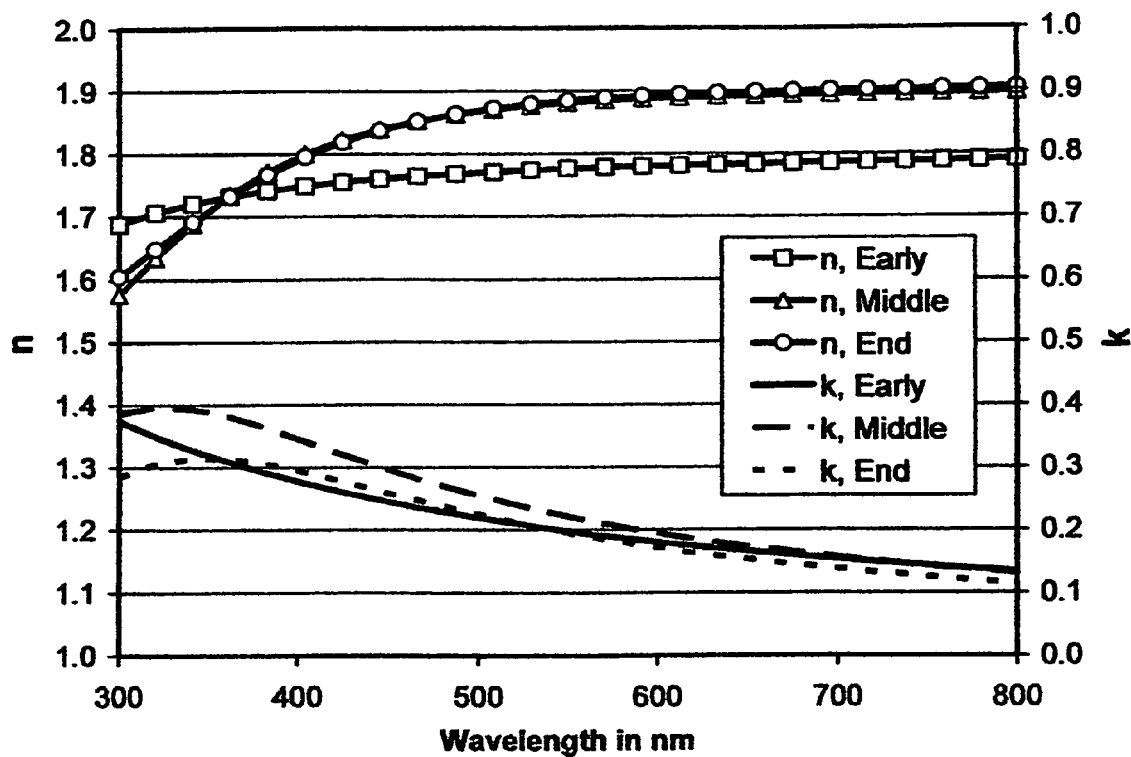
FIG. 6 shows Optical constants extracted from a GenVI analysis of DLC film deposition, during the early, middle, and end stages of deposition. A single Lorentz oscillator was used to model the dispersion, with 4 fit parameters, namely amplitude, energy, broadening, and $\epsilon_\infty$.
Figure 7:
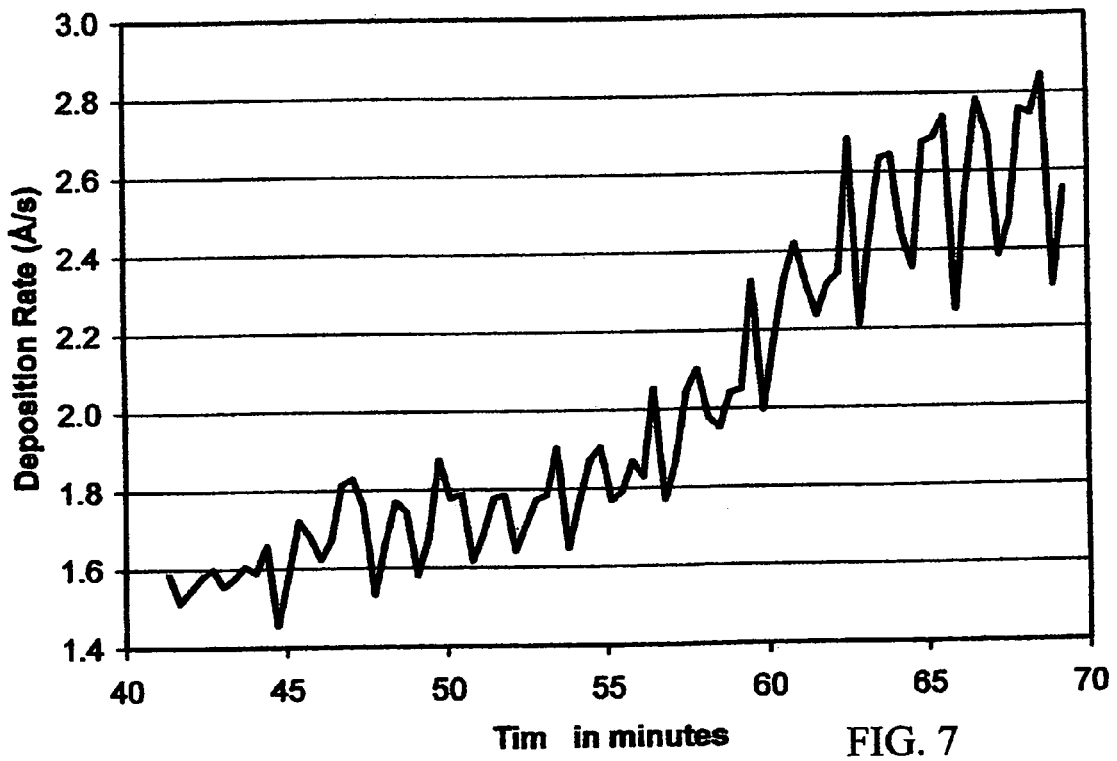
FIG. 7 shows Deposition rate extracted by a GenVI analysis of in situ SE data acquired during a DLC film depositions. The data supplied to the GenVI algorithm at each deposition time was defined by a "sliding window" which included ≈6 minutes of data.
Figure 8:
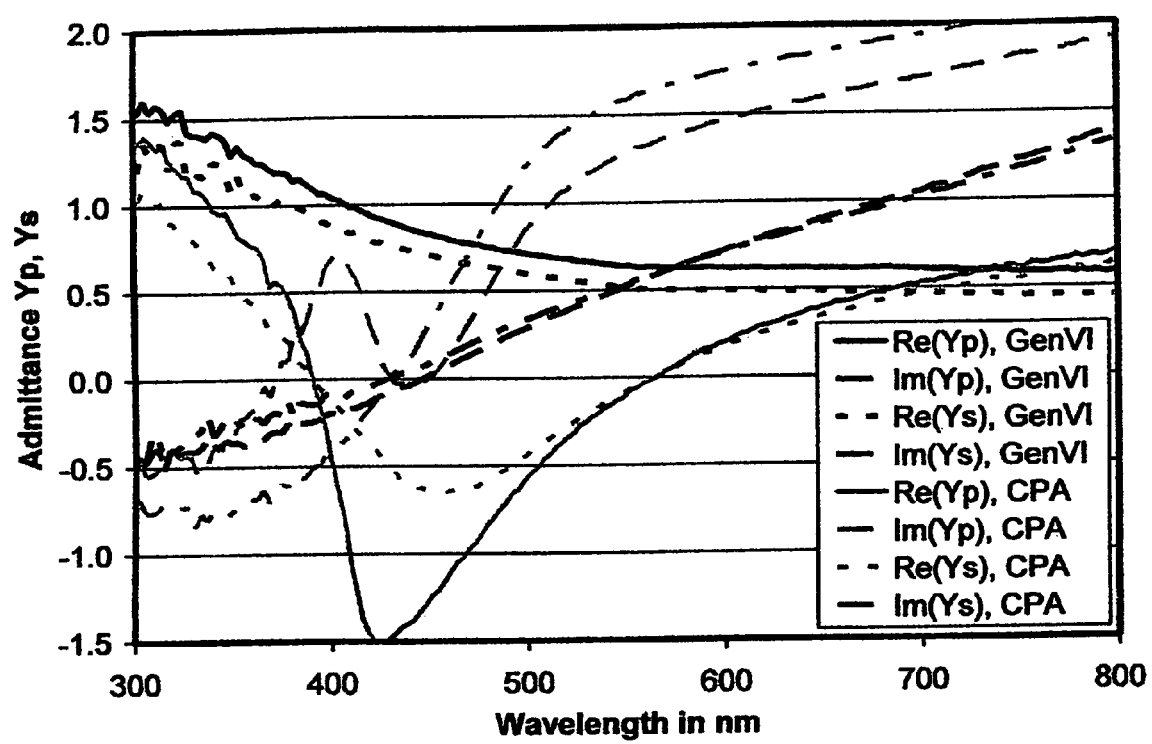
FIG. 8 shows Virtual interface (VI) admittance parameters for p- and s-polarized light for a DLC film near the middle of deposition, calculated using the common pseudo-substrate approximation, (the CPA grey curves), and a general virtual interface, (the GenVI dark curves) analysis.

An example of a general VI analysis, using the Four (4) point algorithm, is shown in FIG. 5. This in situ SE data was acquired during the PECVD deposition of a mixed phase CrC-DLC (diamond-like carbon), film, which was deposited on a NiCr-plated stainless steel ring, (114 mm diameter), which served as a witness sample for the Spectroscopic Ellipsometry measurement. The witness sample was continuously moving and rotating on a planetary table at 3 rpm (see FIG. 4), such that the ellipsometer beam only could see the sample once for less than 0.5 seconds during the rotation period of 20 seconds. A high speed rotating compensator ellipsometer (RCE) with a CCD-based spectrograph detection system, (see Background reference [24]), was used to acquire data over a 250 800 nm spectral range, with a minimum acquisition time of 21 ms. The ellipsometer data acquisition was self-triggered, that is, an ellipsometric data point was acquired only when the detected light intensity exceeded a threshold value. In addition to causing substantial noise, the moving witness sample also limited the time resolution in the data. A substantial (>50 Å) film thickness could deposit while the sample was not in view, which corresponds to a significant fraction of an optical interference cycle. This essentially precludes any derivative-based analysis approach of the data. To obtain acceptable results, the general VI analysis was performed over relatively large time ranges, such as the ≈6 minute windows shown in FIG. 5. The 4 data points incorporated into the GenVI analysis were evaluated at 4 times equally spaced across the 6 minute window. Each of the 4 GenVI points were derived from N, C, and S values at the nearest 5 experimental data times, using a 2nd order smoothing polynomial. The data are best visualized when plotted in terms of N, C, and S (defined in eqn. 7), as these quantities are bounded between ±1 and exhibit more continuous behavior during the deposition of transparent films, as compared to other ellipsometric quantities $\Psi/\Delta$, or the real and imaginary parts of ($\rho$). Note that the GenVI data fits accurately describe the experimental data at all wavelengths throughout the entire deposition. At the shorter wavelengths, the film transitions from transparent to absorbing, while the film remains transparent throughout the deposition at the longer wavelengths. Even with the coarse time/depth resolution, very useful deposition information can be obtained from the GenVI analysis of the in situ SE data. Changes in the optical properties of the film were observed throughout the deposition, as shown in FIG. 6. The film deposition rate also increased dramatically as the run proceeded (FIG. 7), even though the deposition parameters were held constant. Unintentional variations in the deposition conditions, due to effects such as target poisoning, may be responsible for the changes observed in the film properties. To illustrate the inadequacy of the common pseudo-substrate approximation (CPA) in this application (DLC film deposited on metal), virtual interface admittance parameters for a data set near the middle of film deposition were determined using the CPA and a GenVI analysis. Conceptually, the CPA is very simple, the ellipsometric data acquired at the virtual interface is analytically inverted into "pseudo" optical constants (using the standard formula given in eqn. 16, (see Background reference [22])), which are then used as the optical constants for a pseudo-substrate in the optical model that "approximately" encapsulates the optical response of the underlying film structure. From FIG. 8 it is apparent that compared to the GenVI, the CPA calculates dramatically different admittance values for this data set, which explains why attempts to analyze the data using the CPA approach were not successful. The GenVI and CPA calculated admittances converge only when the sample structure consists essentially of a process substrate with a thin layer (at the beginning of the run), and when the film becomes more opaque, and therefore optically looks more like a process substrate near the end of the run.

$$\langle \varepsilon \rangle = \qquad (16)$$
$$\langle \varepsilon_1 \rangle + i \langle \varepsilon_2 \rangle = \langle \tilde{n} \rangle^2 = (\langle n \rangle + i \langle k \rangle)^2 = \sin(\phi)^2 \cdot \left[ 1 + \tan(\phi)^2 \cdot \left( \frac{1-\rho}{1-\rho} \right)^2 \right]$$

Figure 9:
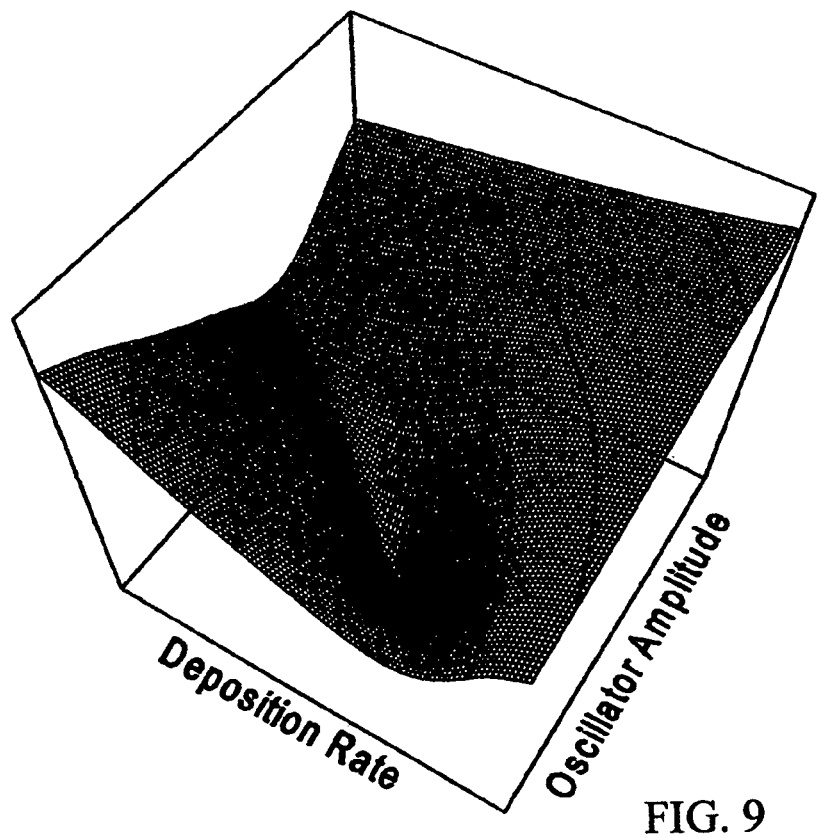
FIG. 9. shows a Plot of the $\chi^2$ error surface vs. deposition rate and Lorentz oscillator amplitude for a 4-point spectroscopic GenVI analysis near the end of the DLC run. The deposition rate was varied from 0.5-3/s with the best fit value being 2.25, and the oscillator amplitude was varied from 0-3 with the best fit value being 1.35).

In contrast to the virtual interface analysis described by Urban, (see Background reference [13]), which in some cases required trial and error or a neural network to obtain acceptable initial estimates for the virtual interface parameters, the presently disclosed invention GenVI analysis of the in situ DLC film data set was found to be quite robust. In most cases, initial values for the Five (5) fit parameters, (deposition rate plus four (4) Lorentz oscillator parameters), could be varied by more than a factor of two and subsequent GenVI model fits would still converge to the same solution. FIG. 9 shows a plot of the $\chi^2$ error surface for a data set near the end of the deposition run, when two of the parameters, (deposition rate and Lorentz oscillator amplitude), were varied, with the other oscillator parameters held fixed at their best fit value. The error surface varies smoothly and exhibits a single minimum; both of these properties are required for robust model fit convergence. This is somewhat surprising, given that the GenVI calculation could potentially choose the wrong "root" for the VI admittances when the film parameters are far from their correct values. Such "root hopping" could lead to a discontinuous error surface, especially when using the 3-point GenVI algorithm and ellipsometric data at only a single wavelength. The Four (4)-point GenVI algorithm combined with spectroscopic ellipsometric (SE) data appears to minimize this behavior.

It is noted that the terminology "process substrate" indicates a substrate per se., as well as a substrate after some processing has been performed thereupon.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

I claim:

1. A method of fabricating and characterizing the outermost material of an article which is manufactured by the deposition or removal of material, to or from, a process substrate, without explicit knowledge of any previously deposited underlying layers, said method comprising a procedure which comprises steps a, a', b and c, said steps a, a', b and c being:
   a) providing a material deposition or removal chamber and an ellipsometer system configured with respect thereto so as to, in use, cause a beam of polarized electromagnetic radiation to impinge upon a process substrate therewithin during a procedure in which material deposition or removal upon said process substrate is caused to occur over a period of time;
   a') obtaining ellipsometric data during material deposition or removal upon said process substrate at three distinct times (t1), (t2), and (t3);
   b) using a system of analytic equations which are derived from the exact Fresnel equations that describe the interaction of electromagnetic radiation with a layered material system, such analytic equations not requiring any knowledge of the underlying layer structure previously deposited on the sample, calculating ellipsometric data at time (t3), using the ellipsometric data acquired at times (t1) and (t2), and a parameterized optical model for the outermost material deposition or removal that occurs between (t1) and (t3), and (t2) and (t3);
   c) determining the optical model parameters which characterize the outermost layer(s) by minimizing the difference between the ellipsometric data calculated at time (t3) by the analytical equations in b) and the ellipsometric data measured at time (t3), using a minimization algorithm; and
   d) practicing said procedure steps a, a', b and c to the end that said article is manufactured and said outermost material thereof is characterized.

2. A method as in claim 1 in which the minimization algorithm is implemented by non-linear regression.

3. A method as in claim 1 in which the minimization algorithm is the Levenberg-Marquardt method.

4. A method as in claim 1 in which the optical model for the outermost material deposition or removal is parameterized by at least one of the parameters from the selected list:
   the material deposition rate,
   the material removal rate,
   the optical constants of the outermost material,
   the surface roughness of the outermost material.

5. A method as in claim 1 in which the substrate is of a shape selected from the group consisting of:
   comprising a planar surface;
   of an arbitrary shape.

6. A method as in claim 1 in which the obtained ellipsometric data is characterized by at least one selection from the group consisting of:
   it is acquired at a single wavelength;
   it is acquired at a more than one wavelength;
   it is acquired at a single angle of incidence;
   it is acquired at least two angles of incidence.

7. A method of fabricating and characterizing the outermost material of an article which is manufactured by the deposition or removal of material, to or from, a process substrate, without explicit knowledge of any previously deposited underlying layers, said method comprising a procedure which comprises steps a, a', b and c, said steps a, a', b and c being:
   a) providing a material deposition or removal chamber and an ellipsometer system configured with respect thereto so as to, in use, cause a beam of polarized electromagnetic radiation to impinge upon a process substrate therewithin during a procedure in which material deposition or removal upon said process substrate is caused to occur over a period of time;

a') obtaining ellipsometric data during material deposition or removal upon said process substrate at four distinct times (t1), (t2), (t3), and (t4);

b) using a system of analytic equations which are derived from the exact Fresnel equations that describe the interaction of electromagnetic radiation with a layered material system, such analytic equations not requiring any knowledge of the underlying layer structure previously deposited on the sample, calculating ellipsometric data:

at time (t1), using the ellipsometric data acquired at times (t2) and (t4), and a parameterized optical model for the outermost material deposition or removal that occurs between (t1) and (t2), and (t1) and (t4);

at time (t2), using the ellipsometric data acquired at times (t1) and (t3), and a parameterized optical model for the outermost material deposition or removal that occurs between (t2) and (t1), and (t2) and (t3);

at time (t3), using the ellipsometric data acquired at times (t2) and (t4), and a parameterized optical model for the outermost material deposition or removal that occurs between (t3) and (t2), and (t3) and (t4);

at time (t4), using the ellipsometric data acquired at times (t1) and (t3), and a parameterized optical model for the outermost material deposition or removal that occurs between (t4) and (t1), and (t4) and (t3);

c) determining the optical model parameters which characterize the outermost layer(s) by minimizing the differences between the ellipsometric data calculated at times (t1), (t2), (t3), and (t4) by the analytical equations in b) and the ellipsometric data measured at times (t1), (t2), (t3), and (t4) using a minimization algorithm; and d) practicing said procedure steps a, a', b and c to the end that said article is manufactured and said outermost material thereof is characterized.

8. A method as in claim 7 in which the minimization algorithm is implemented by non-linear regression.

9. A method as in claim 7 in which the minimization algorithm is the Levenberg-Marquardt method.

10. A method as in claim 7 in which the optical model for the outermost material deposition or removal is parameterized by at least one of the parameters from the selected list:
the material deposition rate,
the material removal rate,
the optical constants of the outermost material,
the surface roughness of the outermost material.

11. A method as in claim 7 in which the substrate is of a shape selected from the group consisting of:
comprising a planar surface;
of an arbitrary shape.

12. A method as in claim 7 in which the obtained ellipsometric data is characterized by at least one selection from the group consisting of:
it is acquired at a single wavelength;
it is acquired at a more than one wavelength;
it is acquired at a single angle of incidence;
it is acquired at least two angles of incidence.

13. A method of fabricating and characterizing the outermost material of an article which is manufactured by the deposition or removal of material, to or from, a process substrate, without explicit knowledge of any previously deposited underlying layers, comprising a procedure which comprises steps a, a', b and c, said steps a, a', b and c being:

a) providing a material deposition or removal chamber and an ellipsometer system configured with respect thereto so as to, in use, cause a beam of polarized electromagnetic radiation to impinge upon a process substrate therewithin during a procedure in which material deposition or removal upon said process substrate is caused to occur over a period of time;

a') obtaining ellipsometric data during material deposition or removal upon said process substrate at least three distinct times {t1, t2, t3 . . . tn};

b) using a system of analytic equations which are derived from the exact Fresnel equations that describe the interaction of electromagnetic radiation with a layered material system, such analytic equations not requiring any knowledge of the underlying layer structure previously deposited on the sample, calculating ellipsometric data:

at one time selected from the set of ellipsometric data points chosen in a'), using the ellipsometric data acquired at two other times from the set of ellipsometric data points chosen in a'), and a parameterized optical model for the outermost material deposition or removal that occurs between the selected times; optionally at additional times selected from the set of ellipsometric data points chosen in a'), using the ellipsometric data acquired at two other times from the set of ellipsometric data points chosen in a'), and a parameterized optical model for the outermost material deposition or removal that occurs between the selected times;

c) determining the optical model parameters which characterize the outermost layer(s) by minimizing the differences between the ellipsometric data calculated at the selected times by the analytical equations in b) and the ellipsometric data measured at the selected times using a minimization algorithm; and d) practicing said procedure steps a, a', b and c to the end that said article is manufactured and said outermost material thereof is characterized.

14. A method as in claim 13 in which the minimization algorithm is implemented by non-linear regression.

15. A method as in claim 13 in which the minimization algorithm is the Levenberg-Marquardt method.

16. A method as in claim 13 in which the optical model for the outermost material deposition or removal is parameterized by at least one of the parameters from the selected list:
the material deposition rate,
the material removal rate,
the optical constants of the outermost material,
the surface roughness of the outermost material.

17. A method as in claim 13 in which the substrate is of a shape selected from the group consisting of:
comprising a planar surface;
of an arbitrary shape.

18. A method as in claim 13 in which the obtained ellipsometric data is characterized by at least one selection from the group consisting of:
it is acquired at a single wavelength;
it is acquired at a more than one wavelength;
it is acquired at a single angle of incidence;
it is acquired at least two angles of incidence.

19. A method of manufacturing and ellipsometrically characterizing surface material present on an article manufactured by the deposition or removal of material, to or from, a process substrate, said method requiring no explicit knowledge of prior process substrate composition;

said method comprising a procedure which comprises steps a, a', a", b, c and d, said steps a, a', a", b, c and d being:
- a) providing a material deposition and/or removal chamber, and an ellipsometer system configured with respect thereto so as to, in use, cause a beam of electromagnetic radiation to impinge upon an article therewithin during a procedure in which material deposition to, or removal from, a process substrate is caused to occur over a period of time:
- a') at least two times causing said ellipsometer system to cause a beam of electromagnetic radiation to impinge upon the article such that sufficient ellipsometric data to evaluate variable parameters which characterize the optical response of the article;
- a") in conjunction with the foregoing steps, providing a system of variable parameter containing analytic equations which describe interaction of electromagnetic radiation with a layered material system;
- b) utilizing said sufficient ellipsometric data obtained in step a' and said system of variable parameter containing analytic equations provided in a", to predict ellipsometric characterization of said article at a prediction time which is different from either of said at least two times of step a';
- c) during material deposition or removal, to or from, a process substrate, obtaining ellipsometric data at a time corresponding to the prediction time of step b; and
- d) utilizing said ellipsometric data obtained in step c in a minimization algorithm to provide values for the variable parameters in at least one selection from the group consisting of:
  - said variable parameters in said variable parameter containing analytic equations which describe interaction of electromagnetic radiation with a layered material system provided in step a"; and
  - said variable parameters identified in step a' which characterized the optical response of the article;
- at said prediction time in step b;
- and interpreting the resulting values for said variable parameters to characterize surface material of said article at the time data was obtained in step c; and
- e) practicing said procedure steps a, a', a", b, c and d to the end that said article is manufactured and said outermost material thereof is ellipsometrically characterized.

20. A method as in claim 19 in which the minimization algorithm is implemented by non-linear regression.

21. A method as in claim 19 in which the minimization algorithm is the Levenberg-Marquardt method.

22. A method as in claim 19 in which the optical model for the outermost material deposition or removal is parameterized by at least one of the parameters from the selected list:
- the material deposition rate,
- the material removal rate,
- the optical constants of the outermost material,
- the surface roughness of the outermost material.

23. A method as in claim 19 in which the substrate is of a shape selected from the group consisting of:
- comprising a planar surface;
- of an arbitrary shape.

24. A method as in claim 19 in which the obtained ellipsometric data is characterized by at least one selection from the group consisting of:
- it is acquired at a single wavelength;
- it is acquired at a more than one wavelength;
- it is acquired at a single angle of incidence;
- it is acquired at least two angles of incidence.

* * * * *